United States Patent
Sato et al.

[11] 4,007,189
[45] Feb. 8, 1977

[54] PYRROLOTRIAZOLOPYRIMIDINE DERIVATIVES AND PROCESS FOR THE PREPARATION THEREOF

[75] Inventors: Yasunobu Sato; Hiromu Takagi; Yasuo Shimoji; Seiji Kumakura, all of Tokyo, Japan

[73] Assignee: Sankyo Company Limited, Tokyo, Japan

[22] Filed: May 4, 1976

[21] Appl. No.: 683,055

[30] Foreign Application Priority Data

May 31, 1975 Japan .................................. 50-65832

[52] U.S. Cl. ..................... 260/256.4 F; 424/251
[51] Int. Cl.² ..................................... C07D 487/14
[58] Field of Search .......................... 260/256.4 F

[56] References Cited
UNITED STATES PATENTS 3,769,288  10/1973  Stahale et al. ............ 260/256.4 F
3,868,374   2/1975  Yale et al. ................ 260/256.4 F Primary Examiner—Donald G. Daus
Assistant Examiner—James H. Turnipseed
Attorney, Agent, or Firm—Flynn & Frishauf

[57] ABSTRACT

Pyrrolotriazolopyrimidine derivatives having the formula

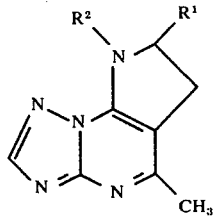

wherein $R^1$ represents hydrogen atom or an alkyl group having from 1 to 4 carbon atoms and $R^2$ represents an alkyl group having from 1 to 4 carbon atoms, a cycloalkyl group having from 5 to 8 carbon atoms, a phenyl group optionally substituted with one or more halogen atoms or a phenylalkyl group having the formula

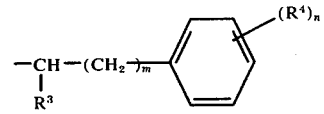

in which $R^3$ represents hydrogen atom or an alkyl group having from 1 to 4 carbon atoms, $R^4$ represents halogen atom, an alkyl group having from 1 to 4 carbon atoms or an alkoxy group having from 1 to 4 carbon atoms, $m$ represents an integer from 0 to 2 and $n$ represents an integer from 0 to 3, and pharmacologically acceptable salts thereof. The compounds are useful as vasodilating or hypotensive agents and may be prepared by reacting triazolopyrimidine derivatives having the formula

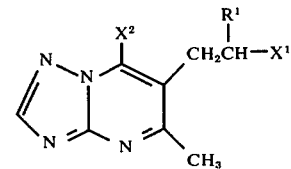

wherein $X^1$ and $X^2$ may be the same or different and each represents a halogen atom and $R^1$ has the same meaning as defined above with an amine having the formula

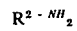

wherein $R^2$ has the same meaning as defined above.

10 Claims, No Drawings

PYRROLOTRIAZOLOPYRIMIDINE DERIVATIVES AND PROCESS FOR THE PREPARATION THEREOF

This invention relates to novel pyrrolotriazolopyrimidines and a process for the preparation thereof.

More particularly, it relates to pyrrolotriazolopyrimidines having the formula

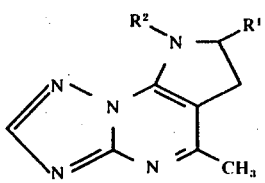

(I)

wherein $R^1$ represents hydrogen atom or an alkyl group having from 1 to 4 carbon atoms and $R^2$ represents an alkyl group having from 1 to 4 carbon atoms, a cycloalkyl group having from 5 to 8 carbon atoms, a phenyl group optionally substituted with one or more halogen atoms or a phenylalkyl group having the formula

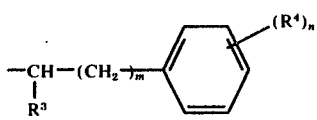

in which $R^3$ represents hydrogen atom or an alkyl group having from 1 to 4 carbon atoms, $R^4$ represents a halogen atom, an alkyl group having from 1 to 4 carbon atoms or an alkoxy group having from 1 to 4 carbon atoms, $m$ represents an integer from 0 to 2 and $n$ represents an integer from 0 to 3 and their pharmacologically acceptable salts and also relates to a process for the preparation thereof.

In the above formula (I), $R^1$ is preferably hydrogen atom or a straight or branched alkyl group having from 1 to 4 carbon atoms, for example, methyl, ethyl, n-propyl, isopropyl, n-butyl and isobutyl. $R^2$ preferably represents a straight or branched alkyl group having from 1 to 4 carbon atoms, for example, methyl, ethyl, n-propyl, isopropyl, n-butyl, isobutyl and tertbutyl; a cycloalkyl group having from 5 to 8 carbon atoms, for example, cyclopentyl, cyclohexyl cycloheptyl and cyclooctyl; a phenyl group optionally substituted with one or more halogen atoms, for example, o-, m- or p-chlorophenyl, o-, m- or p-bromophenyl, o-, m- or p-fluorophenyl, 2,4-dichlorophenyl, 2,5-dichlorophenyl, 2,6-dichlorophenyl, 2,6-dibromophenyl and 2,6-difluorophenyl. $R^3$ preferably represents hydrogen atom or a straight or branched alkyl group having from 1 to 4 carbon atoms, for example, methyl and ethyl. $R^4$ preferably represents a halogen atom, for example, chlorine, bromine and fluorine; a straight or branched alkyl group having from 1 to 4 carbon atoms, for example, methyl, ethyl, n-propyl and n-butyl; or an alkoxy group having from 1 to 4 carbon atoms, for example, methoxy, ethoxy, n-propoxy and n-butoxy.

We have studied pyrrolotriazolopyrimidine derivatives for many years and have attained this invention upon finding that novel pyrrolotriazolopyrimidine derivatives having the aformentioned formula (I) exhibit vasodilating and hypotensive activities.

According to the process of the invention, compounds of formula (I) can be prepared by reacting a triazolopyrimidine derivative having the formula

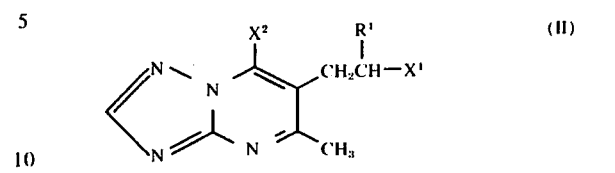

(II)

wherein $X^1$ and $X^2$ may be the same or different and each represents a halogen atom and $R^1$ has the same meaning as defined above, with an amine having the formula $$R^2 - NH_2 \qquad (III)$$

wherein $R^2$ has the same meaning as defined above.

In carrying out the process of this invention, the triazolopyrimidine derivative (II) is contacted with the amine (III), preferably in the presence of an inert solvent.

Preferable examples of the inert solvent include an aromatic hydrocarbon such as benzene, toluene, xylene and the like, an alcohol such as methanol, ethanol, isopropanol and the like, and a dialkylformamide such as dimethylformamide and the like. The reaction temperature is not particularly critical, but the reaction is carried out usually at 50° C to 200° C, preferably near the reflux temperature of the solvent employed. The reaction time may be varied mainly depending upon the kind of starting material, the reaction temperature and the like, but it may usually take about 1 hour to 20 hours.

In addition to the amine of the aforementioned formula (III) employed in this reaction, an inorganic or organic base may be used as an acid binding agent and such an alkali metal carbonate as sodium carbonate, potassium carbonate and the like, or a tert-amine such as triethylamine, are mentioned as examples of preferable acid binding agents.

After the reaction is completed, the product may be recovered by a usual manner from the reaction mixture. For instance, the product may be obtained as a crystalline substance by filtration of the reaction mixture after completion of the reaction, followed by concentration of the filtrate, or, when the product thus obtained is an oily substance, it may be obtained as a crystalline salt as described later.

The product thus obtained may be further purified by a conventional technique such as recrystallization, column chromatography and the like.

A product having the formula (I) may be converted to a pharmacologically acceptable acid addition salt. Examples of the acid to form such acid addition salts include an inorganic acid such as hydrochloric acid, sulfuric acid, phosphoric acid and the like and an organic acid such as oxalic acid, maleic acid, tartaric acid, citric acid, malonic acid and the like.

All of the compounds having the above formula (I) exhibit remarkable vasodilating and hypotensive activities, according to pharmacological tests. The results of the pharmacological tests are shown in the Tables 1 and 2.

Table 1

| Compound | Coronary Vasodilating Activity | |
|---|---|---|
| | Dose mg/kg (dog, i.v) | Coronary Sinus Flow (Relative ratio of area under curve) |
| 8-tert-Butyl-6,7-dihydro-5-methyl-8H-pyrrolo[3,2-e]-s-triazolo[1,5-a]pyrimidine | 0.3<br>1.0 | 4.2<br>9.5 |
| 8-Cyclooctyl-6,7-dihydro-5-methyl-8H-pyrrolo[3,2-e]-s-triazolo[1,5-a]pyrimidine | 1.0 | 1.2 |
| 8-(2,6-Dichlorophenyl)-6,7-dihydro-5-methyl-8H-pyrrolo[3,2-e]-s-triazolo[1,5-a]pyrimidine | 1.0 | 1.5 |
| 8-tert-Butyl-6,7-dihydro-5,7-dimethyl-8H-pyrrolo[3,2-e]-s-triazolo[1,5-a]pyrimidine. hydrochloride | 1.0<br>3.0 | 1.5<br>8.5 |
| 8-(o-Fluorobenzyl)-6,7-dihydro-5-methyl-8H-pyrrolo[3,2-e]-s-triazolo[1,5-e]-pyrimidine | 3.0 | 4.1 |
| 8-(o-Chlorobenzyl)-6,7-dihydro-5,7-dimethyl-8H-pyrrolo[3,2-e]-s-triazolo[1,5-a]pyrimidine | 1.0<br>3.0 | 1.0<br>4.8 |
| 7-Ethyl-8-(o-fluorobenzyl)-6,7-dihydro-5-methyl-8H-pyrrolo[3,2-e]-s-triazolo[1,5-a]pyrimidine | 3.0 | 5.2 |
| 6,7-Dihydro-5-methyl-8-(3,4,5-trimethoxybenzyl)-8H-pyrrolo[3,2-e]-s-triazolo[1,5-a]pyrimidine | 1.0<br>3.0 | 1.4<br>2.2 |
| Control<br>Trapymin | 0.3<br>1.0<br>3.0 | 0.3<br>1.0<br>4.4 |

The coronary vasodilation test utilized here was based on the method of Morawitz [P. Morawitz and A. Zahn, Zentrablatt fur Physiologie, vol. 26, p. 465 (1912); and R. Charlier, Antianginal Drugs (1971), p. 70] using an anesthetized dog.

Table 2

| Compound | Hypotensive Activity | |
|---|---|---|
| | Dose, mg/kg (rat, p.o.) | Hypotensive Index (mmHg.6 hrs) |
| 8-tert-Butyl-6,7-dihydro-5-methyl-8H-pyrrolo[3,2-e]-s-triazolo[1,5-a]pyrimidine | 10 | 125 |
| Control Mecamylamine | 30 | 110 |

The hypotensive activity test utilized here was based on the method reported by Takagi, et al. in Chemical & Pharmaceutical Bulletin, vol. 22, p. 514 (1974), using a spontaneously hypertensive rat.

Accordingly the compounds of the formula (I) have been found to be useful as a vasodilator or hypotensive agent. As administration methods are mentioned, for instance, the oral route in the form of tablet, capsule, granule, powder or syrup, and the parenteral route by injection. The dosage unit is varied depending upon the symptoms, age, body weight of the patient, but a usual unit is in amounts of from about 15mg to 100mg per day for adults in the oral administration, and it may be given once or separately several times a day. In the parenteral administration, 10mg to 50mg of the compound for one injection may be given subcutaneously, intramuscularly or intravenously.

A compound having the formula (II) which is employed as a starting material in the process of the present invention is a novel compound, and can be prepared by reacting a hydroxyethyl-triazolopyrimidine derivative having the formula

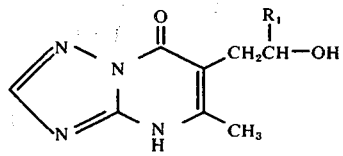

(IV)

wherein $R^1$ has the same meaning as defined above with a phosphorus oxyhalide, for example, phosphorus oxychloride, phosphorus oxybromide and the like in the presence or absence of a solvent. The solvent may be employed without any particular limitation, so far as it does not participate in the reaction. As preferable solvents are mentioned halogenated aliphatic hydrocarbons such as dichloroethane, chloroform and the like. The reaction temperature is not critical, but the reaction is usually carried out at 50° C to 150° C. The reaction time may be varied mainly depending upon the kind of starting material and the reaction temperature employed, but it may usually take about 2 to 5 hours.

After completion of the reaction, the desired product can be recovered by a usual manner from the reaction mixture, and the product thus obtained, if desired, may be further purified by a conventional method such as recrystallization or column chromatography.

The following examples are given for the illustration of this invention.

EXAMPLE 1

6,7-Dihydroxy-5,8-dimethyl-8H-pyrrolo[3,2-e]-s-triazolo[1,5-a]pyrimidine

A mixture of 2g of 7-chloro-6-(2-chloroethyl)-5-methyl-s-triazolo[1,5-a]pyrimidine, 0.67g of 40% aqueous methylamine solution, 4 ml of triethylamine and 20 ml of ethanol was stirred at room temperature for 30 minutes and then refluxed for 1.5 hours. The reaction mixture was concentrated under reduced pressure and the residue was washed with water. The crystals thus obtained were crystallized from ethanol affording 1.05g of colorless needles of m.p. 215° – 217° C.

Elementary analysis for $C_9H_{11}N_5$ Calculated: C, 57.12; H, 5.86; N, 37.02. Found: C, 57.31; H, 5.76; N, 37.33.

According to the same procedure as in Example 1, there were obtained following pyrrolotriazolopyrimidines.

8-Ethyl-6,7-dihydro-5-methyl-8H-pyrrolo[3,2-e]-s-triazolo[1,5-a]pyrimidine m.p. 119° – 120° C Elementary analysis for $C_{10}H_{13}N_5$ Calculated: C, 59.09; H, 6.45; N, 34.46 Found: C, 58.90; H, 6.71; N, 34.12

6,7-Dihydro-5-methyl-8-n-propyl-8H-pyrrolo[3,2-e]-s-triazolo[1,5-a]pyrimidine m.p. 131.5° – 133° C Elementary analysis for $C_{11}H_{15}N_5$ Calculated: C, 60.80; H, 6.96; N, 32.24. Found: C, 60.59; H, 6.95; N, 32.24.

6,7-Dihydro-8-isopropyl-5-methyl-8H-pyrrolo[3,2-e]-s-triazolo[1,5-a]pyrimidine m.p. 189.5° – 190° C Elementary analysis for $C_{11}H_{15}N_5$ Calculated: C, 60.80; H, 6.96; N, 32.24. Found: C, 60.70; H, 6.99; N, 32.05.

8-Cyclohexyl-6,7-dihydro-5-methyl-8H-pyrrolo[3,2-e]-s-triazolo[1,5-a]pyrimidine m.p. 214° – 216° C Elementary analysis for $C_{14}H_{19}N_5$ Calculated: C, 65.34; H, 7.44; N, 27.22 Found: C, 65.47; H, 7.46; N, 27.24

6,7-Dihydro-5-methyl-8-(p-methylbenzyl)-8H-pyrrolo[3,2-e]-s-triazolo[1,5-a]pyrimidine m.p. 200° – 201.5° C Elementary analysis for $C_{16}H_{17}N_5$ Calculated: C, 68.79; H, 6.13; N, 25.07 Found: C, 68.72; H, 5.91; N, 24.97

6,7-Dihydro-5-methyl-8-(p-methoxybenzyl)-8H-pyrrolo-[3,2-e]-s-triazolo[1,5-a]pyrimidine m.p. 172° – 173.5° C Elementary analysis for $C_{16}H_{17}ON_5$ Calculated: C, 65.06; H, 5.80; N, 23.72. Found: C, 65.02; H, 5.77; N, 23.72.

8-(o-Chlorobenzyl)-6,7-dihydro-5-methyl-8H-pyrrolo-[3,2-e]-s-triazolo[1,5-a]pyrimidine m.p. 207° – 208.5° C Elementary analysis for $C_{15}H_{14}N_5Cl$ Calculated: C, 60.10; H, 4.71; N, 23.36; Cl, 11.83. Found: C, 60.28; H, 4.70; N, 23.38; Cl, 11.43.

8-(p-Chlorobenzyl)-6,7-dihydro-5-methyl-8H-pyrrolo[3,2-e]-s-triazolo]1,5-a]pyrimidine m.p. 209.5° – 211° C Elementary analysis for $C_{15}H_{14}N_5Cl$ Calculated: C, 60.10; H, 4.71; N, 23.36; Cl, 11.83. Found: C, 60.27; H, 4.71; N, 23.40; Cl, 11.92.

6,7-Dihydro-8-(o-fluorobenzyl)-5-methyl-8H-pyrrolo[3,2-e]-s-triazoro[1,5-a]pyrimidine m.p. 186° – 187° C Elementary analysis for $C_{15}H_{14}N_5F$ Calculated: C, 63.59; H, 4.98; N, 24.72. Found: C, 63.47; H, 4.97; N, 24.47.

6,7-Dihydro-8-(3,4-dimethoxybenzyl)-5-methyl-8H-pyrrolo[3,2-e]-s-triazolo[1,5-a]pyrimidine m.p. 179° – 180° C Elementary analysis for $C_{17}H_{19}O_2N_5$ Calculated: C, 62.75; H, 5.89; N, 21.53. Found: C, 62.71; H, 5.86; N, 21.30.

6,7-Dihydro-5-methyl-8-(1-phenylethyl)-8H-pyrrolo[3,2-e]-s-triazlo[1,5-a]pyrimidine m.p. 157.5° – 158.5° C Elementary analysis for $C_{16}H_{17}N_5$ Calculated: C, 68.79; H, 6.13; N, 25.07. Found: C, 68.67; H, 6.16; N, 25,07.

6,7-Dihydro-5-methyl-8-(2-phenylethyl)-8H-pyrrolo[3,2-e]-s-triazolo[1,5; -a]pyrimidine m.p. 111°–112° C Elementary analysis for $C_{16}H_{17}N_5$ Calculated: C, 68.79; H, 6.13; N, 25.07. Found: C, 68.56; H, 6.36; N, 25.66.

6,7-Dihydro-8-[2-(3,4-dimethoxyphenyl)ethyl]-5-methyl-8H-pyrrolo[3,2-e]-s-triazolo[1,5-a]pyrimidine m.p. 141.5° – 142° C Elementary analysis for $C_{18}H_{21}O_2N_5$ Calculated: C, 63.70; H, 6.24; N, 29.64. Found: C, 63.50; H, 6.52; N, 20.72.

EXAMPLE 2

8-n-Butyl-6,7-dihydro-5-methyl-8H-pyrrolo[3,2-e]-s-triazolo[1,5-a]pyrimidine

A mixture of 2g of 7-chloro-6-(2-chloroethyl)-5-methyl-s-triazolo[1,5-a]pyrimidine, 0.95g of n-butylamine hydrochloride, 4 ml of triethylamine and 20 ml of ethanol was stirred under reflux for 1 hour. The reaction mixture was then concentrated under reduced pressure and the residue was dissolved in chloroform and purified by an column chromatography of alumina. The crystals thus obtained were recrystallized from isopropyl ether affording 1.35g of pale yellow needles of m.p. 72° – 75° C.

Elementary analysis for $C_{12}H_{17}N_5$ Calculated: C, 62.31; H, 7.41; N, 30.28. Found: C, 61.97; H, 7.38; N, 29.91.

EXAMPLE 3

8-sec-Butyl-6,7-dihydro-5-methyl-8H-pyrrolo[3,2-e]-s-triazolo[1,5-a]pyrimidine

A mixture of 2.3g of 7-chloro-6-(2-chloroethyl)-5-methyl-s-triazolo[1,5-a]pyrimidine, 1g of sec-butylamine, 1.8g of sodium carbonate and 20 ml of ethanol was refluxed for 2 hours. The hot reaction mixture was then filtered and the filtrate was concentrated under reduced pressure.

The residue was recrystallized from water affording 0.6g of pale yellow needles of m.p. 148° – 149° C.

Elementary analysis for $C_{12}H_{17}N_5$ Calculated: C, 62.31; H, 7.41; N, 30.28. Found: C, 62.23; H, 7.29; N, 30.19.

According to the same procedure as in Example 3, there were obtained following pyrrolotriazolopyrimidines.

8-n-Butyl-6,7-dihydro-5,7-dimethyl-8H-pyrrolo[3,2-e]-s-triazolo[1,5-a]pyrimidine m.p. 94.5° – 96.5° C Elementary analysis for $C_{13}H_{19}N_5$ Calculated: C, 63.64; H, 7.81; N, 28.55. Found: C, 63.15; H, 7.75; N, 28.36.

6,7-Dihydro-5,7-dimethyl-8-isopropyl-8H-pyrrolo[3,2-e]-s-triazolo[1,5-a]pyrimidine m.p. 155° – 157° C Elementary analysis for $C_{12}H_{17}N_5$ Calculated: C, 62.31; H, 7.41; N, 30.28. Found: C, 62.35; H, 7.38; N, 30.08.

6,7-Dihydro-5,7-dimethyl-8-(p-methoxybenzyl)-8H-pyrrolo[3,2-e]-s-triazolo[1,5-a]pyrimidine m.p. 144° – 145° C Elementary analysis for $C_{17}H_{19}ON_5$ Calculated: C, 66.00; H, 6.19; N, 22.64. Found: C, 66.29; H, 6.22; N, 22.48.

8-(o-Chlorobenzyl)-6,7-dihydro-5,7-dimethyl-8H-pyrrolo[3,2-e]-s-triazolo[1,5-a]pyrimidine m.p. 153° – 155° C Elementary analysis for $C_{16}H_{16}N_5Cl$ Calculated: C, 61.24; H, 5.14; N, 22.32; Cl, 11.30. Found: C, 61.46; H, 5.05; N, 22.15; Cl, 11.46.

6,7-Dihydro-5,7-dimethyl-8-(o-fluorobenzyl)-8H-pyrrolo[3,2-e]-s-triazolo[1,5-a]pyrimidine m.p. 149° – 150° C Elementary analysis for $C_{16}H_{16}N_5F$ Calculated: C, 64.63; H, 5.42; N, 23.55; F, 6.39. Found: C, 64.52; H, 5.49; N, 23.58; F, 6.58.

6,7-Dihydro-7-ethyl-8-isopropyl-5-methyl-8H-pyrrolo[3,2-e]-s-triazolo[1,5-a]pyrimidine m.p. 142° – 143° C Elementary analysis for $C_{13}H_{19}N_5$ Calculated: C, 63.64; H, 7.81; N, 28.55. Found: C, 63.56; H, 7.85; N, 28.35.

8-n-Butyl-6,7-dihydro-7-ethyl-5-methyl-8H-pyrrolo[3,2-e]-s-triazolo[1,5-a]pyrimidine m.p. 75° – 76.5° C Elementary analysis for $C_{14}H_{21}N_5$ Calculated: C, 64.83; H, 8.16; N, 27.01. Found: C, 64.89; H, 8.25; N, 26.88.

6,7-Dihydro-7-ethyl-8-(o-fluorobenzyl)-5-methyl-8H-pyrrolo[3,2-e]-s-triazolo[1,5-a]pyrimidine m.p. 117° – 118° C Elementary analysis for $C_{17}H_{18}N_5F$ Calculated: C, 65.58; H, 5.83; N, 22.49; F, 6.10 Found: C, 65.96; H, 5.58; N, 22.51; F, 6.08.

6,7-Dihydro-5-methyl-8-(3,4,5-trimethoxybenzyl)-8H-pyrrolo[3,2-e]-s-triazolo[1,5-a]pyrimidine m.p. 193° – 194° C Elementary analysis for $C_{18}H_{21}O_3N_5$ Calculated: C, 60.83; H, 5.96; N, 19.71. Found: C, 60.77; H, 5.88; N, 19.62.

EXAMPLE 4

6,7-Dihydro-8-isobutyl-5-methyl-8H-pyrrolo[3,2-e]-s-triazolo[1,5-a]pyrimidine

A mixture of 2.3g of 7-chloro-6-(2-chloroethyl)-5-methyl-s-triazolo[1,5-a]pyrimidine, 1g of isobutylamine, 1.8g of sodium carbonate and 20 ml of ethanol was treated by the same manner as described in Example 3. The crystals thus obtained were recrystallized from aqueous methanol to give 1.4g of pale yellow prisms of m.p. 143° – 145° C.

Elementary analysis for $C_{12}H_{17}N_5$ Calculated: C, 62.31; H, 7.41; N, 30.28. Found: C, 62.08; H, 7.35; N, 30.28.

EXAMPLE 5

8-tert-Butyl-6,7-dihydro-5-methyl-8H-pyrrolo[3,2-e]-s-triazolo[1,5-a]pyrimidine

A mixture of 4.5g of 7-chloro-6-(2-chloroethyl)-5-methyl-s-triazolo[1,5-a]pyrimidine, 1.47g of tert-butylamine, 10 ml of triethylamine and 20 ml of ethanol was stirred under reflux for 5 hours. Ethanol was then removed from the reaction mixture under reduced pressure, water was added to the residue, the mixture was adjusted to pH 9 by an addition of 10% aqueous sodium carbonate solution and extracted with chloroform. The extract was concentrated under reduced pressure and the residue was purified by silica gel chromatography. The crystals thus obtained were recrystallized from a mixture of isopropylether and tetrahydrofuran affording 1.85g of pale yellow prisms of m.p. 177.5° – 178° C.

Elementary analysis for $C_{12}H_{17}N_5$ Calculated: C, 62.31; H, 7.41; N, 30.28. Found: C, 62.54; H, 7.46; N, 30.41.

The hydrochloride · trihydrate colorless needles, m.p. 245° C(decom.) (from isopropanol)

Elementary analysis for $C_{12}H_{18}N_5Cl.3H_2O$ Calculated: C, 44.79; H, 7.52; N, 21.76; Cl, 11.02. Found: C, 45.07; H, 7.67; N, 21.39; Cl, 11.07.

EXAMPLE 6

8-Cycloheptyl-6,7-dihydro-5-methyl-8H-pyrrolo[3,2-e]-s-triazolo[1,5-a]pyrimidine A mixture of 2g of 7-chloro-6-(2-chloroethyl)-5-methyl-s-triazolo[1,5-a]pyrimidine, 0.98g of cycloheptylamine, 3 ml of triethylamine and 20 ml of ethanol was stirred under reflux for 1.5 hours and treated thereafter as described in Example 5. The crystals thus obtained were crystallized from tetrahydrofuranisopropyl ether to give 1.4g of pale yellow needles of m.p. 197° – 198° C.

Elementary analysis for $C_{15}H_{21}N_5$ Calculated: C, 66.39; H, 7.80; N, 25.81. Found: C, 66.40; H, 7.74; N, 25.61.

EXAMPLE 7

8-Cyclooctyl-6,7-dihydro-5-methyl-8H-pyrrolo[3,2-e]-s-triazolo[1,5-a]pyrimidine

A mixture of 2g of 7-chloro-6-(2-chloroethyl)-5-methyl-s-triazolo[1,5-a]pyrimidine, 1.45g of cyclooctylamine hydrochloride, 4 ml of triethylamine and 20 ml of isopropyl alcohol was stirred under reflux for 1.5 hours, and treated thereafter as described in Example 5. The crystals thus obtained were recrystallized from ethanol to give 1.25g of colorless needles of m.p. 188.5° – 190.5° C.

Elementary analysis for $C_{16}H_{23}N_5$ Calculated: C, 67.33; H, 8.12; N, 24.54. Found: C, 67.16; H, 8.21; N, 24.62.

EXAMPLE 8

8-Benzyl-6,7-dihydro-5-methyl-8H-pyrrolo[3,2-e]-s-triazolo[1,5-a]pyrimidine

A mixture of 2g of 7-chloro-6-(2-chloroethyl)-5-methyl-s-triazolo[1,5-a]pyrimidine, 0.94g of benzylamine, 3 ml of triethylamine and 20 ml of ethanol was stirred under reflux for 1 hour. The reaction mixture was then concentrated under reduced pressure and the residue was washed with water. The crystals thus obtained were recrystallized from ethanol to give 1.4g of colorless prisms of m.p. 170.5° – 172° C.

Elementary analysis for $C_{15}H_{15}N_5$ Calculated: C, 67.90; H, 5.70; N, 26.40. Found: C, 68.16; H, 5.55; N, 26.60.

EXAMPLE 9

8-(2,6-Dichlorophenyl)-6,7-dihydro-5-methyl-8H-pyrrolo[3,2-e]-s-triazolo[1,5-a]pyrimidine A mixture of 2g of 7-chloro-6-(2-chloroethyl)-5-methyl-s-triazolo[1,5-a]pyrimidine and 1.45g of 2,6-dichloroaniline was stirred for 30 minutes at 190° – 200° C.

To the reaction mixture were added an aqueous solution of potassium carbonate and chloroform, the chloroform layer was separated and subjected to silica gel chromatography for purification. The crystals thus obtained were recrystallized from tetrahydrofuranisopropyl ether to give 1.08g of coloroless needles of m.p. 192.5° – 193.5° C.

Elementary analysis for $C_{14}H_{11}N_5Cl_2$ Calculated: C, 52.52; H, 3.46; N, 21.87; Cl, 22.15. Found: C, 52.99; H, 3.44; N, 21.86; Cl, 22.05.

EXAMPLE 10

8-tert-Butyl-6,7-dihydro-5,7-dimethyl-8H-pyrrolo[3,2-e]-s-triazolo[1,5-a]pyrimidine Hydrochloride A mixture of 2.4g of 7-chloro-6-(2-chloropropyl)-5-methyl-s-triazolo[1,5-a]pyrimidine, 0.9g of tert-butylamine, 1.8g of sodium carbonate and 20 ml of ethanol was stirred for 3 hours at room temperature and then refluxed for 5 hours. The hot reaction mixture was filtered, the filtrate was concentrated under reduced pressure and the residue was purified by a column chromatography of alumina. To an oily substance thus obtained was added a solution of hydrogen chloride-ethanol and the crystals precipitated thereby were collected by filtration.

Recrystallization of the product from isopropyl alcohol-isopropyl ether afforded 110mg of colorless needles of m.p. 178°–180° C (decomp.).

Elementary analysis for $C_{13}H_{19}N_5 \cdot HCl$ Calculated: C, 55.43; H, 7.16; N, 24.86; Cl, 12.59. Found: C, 55.54; H, 7.42; N, 24.60; Cl, 12.61.

EXAMPLE 11

8-tert-Butyl-6,7-dihydro-7-ethyl-5-methyl-8H-pyrrolo[3,2-e]-s-triazolo[1,5-a]pyrimidine Hydrochloride Hydrate A mixture of 2.6g of 7-chloro-6-(2-chlorobutyl)-5-methyl-s-triazolo[1,5-a]pyrimidine, 0.9g of tertbutylamine, 1.8g of sodium carbonate and 20 ml of ethanol was stirred at room temperature for 1 hour and then refluxed for 5 hours. The reaction mixture was thereafter treated by the same manner as described in Example 10. The crystals thus obtained were recrystallized from isopropyl alcohol-isopropyl ether to give 400 mg of pale yellow crystals of m.p. 170° C (decomp).

Elementary analysis for $C_{14}H_{21}N_5 \cdot HCl \cdot H_2O$ Calculated: C, 53.58; H, 7.71; N, 22.32; Cl, 11.30. Found: C, 53.58; H, 7.79; N, 22.18; Cl, 11.10.

Preparation of the starting materials (II)

7-Chloro-6-(2-chloroethyl)-5-methyl-s-triazolo[1,5-a]pyrimidine

A mixture of 85g of 6-(2-hydroxyethyl)-5-methyl-s-triazolo[1,5-a]pyrimidine-7(4H)-one and 201g of phosphorus oxychloride was stirred under reflux for 3 hours. The reaction mixture was then concentrated under reduced pressure and the residue was poured into ice-water. The crystals thus precipitated were collected by filtration, washed with water and recrystallized from tetrahydrofuran-isopropyl ether affording 79g of colorless crystals of m.p. 81° – 82° C.

Elementary analysis for $C_8H_8N_4Cl_2$ Calculated: C, 41.58; H, 3.49; N, 24.25; Cl, 30.68. Found: C, 41.65; H, 3.73; N, 24.21; Cl, 30.41.

According to the same procedure as described above, there were obtained following hydroxyethyl-triazolopyrimidine derivatives.

7-Chloro-6-(2-chloropropyl)-5-methyl-s-triazolo[1,5-a]pyrimidine m.p. 77° – 78° C Elementary analysis for $C_9H_{10}N_4Cl_2$ Calculated: C, 44.10; H, 4.11; N, 22,86; Cl, 28.93. Found: C, 44.33; H, 4.28; N, 22.75; Cl, 28.56.

7-Chloro-6-(2-chlorobutyl)-5-methyl-s-triazolo[1,5a]pyrimidine m.p. 109° – 110° C.

Elementary analysis for $C_{10}H_{12}N_4Cl_2$ Calculated: C, 46.35; H, 4.67; N, 21.62; Cl, 27.36. Found: C, 46.50; H, 4.71; N, 21.76; Cl, 27.01.

I claim:
1. A pyrrolotriazolopyrimidine having the formula

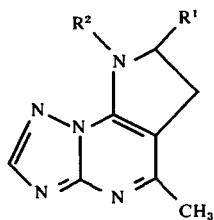

wherein $R^1$ represents hydrogen or alkyl having from 1 to 4 carbon atoms and $R^2$ represents alkyl having from 1 to 4 carbon atoms, cycloalkyl having from 5 to 8 carbon atoms, phenyl, phenyl substituted with halogen selected from the group consisting of fluorine, chlorine or bromine, or a phenylalkyl having the formula

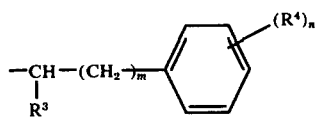

in which $R^3$ represents hydrogen or alkyl having from 1 to 4 carbon atoms, $R^4$ represents halogen selected from the group consisting of fluorine, chlorine or bromine, alkyl having from 1 to 4 carbon atoms or alkoxy having from 1 to 4 carbon atoms, m represents an integer from 0 to 2 and n represents an integer from 0 to 3, and pharmacologically acceptable salts thereof.

2. A pyrrolotriazolopyrimidine as claimed in claim 1 wherein $R^1$ represents hydrogen, methyl or ethyl, $R^2$ represents methyl, ethyl, n-propyl, isopropyl, n-butyl, sec-butyl, isobutyl, t-butyl, cyclohexyl, cycloheptyl, cyclooctyl, chlorophenyl, benzyl, phenethyl or phenethyl substituted with from one to three methyl chlorine, fluorine or methoxy in the benzene ring.

3. 8-tert-Butyl-6,7-dihydro-5-methyl-8H-pyrrolo[3,2-e]-s-triazolo[1,5-a]pyrimidine.

4. 8-Cyclooctyl-6,7-dihydro-5-methyl-8H-pyrrolo[3,2-e]-s-triazolo[1,5-a]pyrimidine.

5. 8-(2,6-Dichlorophenyl)-6,7-dihydro-5-methyl-8H-pyrrolo[3,2-e]-s-triazolo[1,5-a]pyrimidine.

6. 8-tert-Butyl-6,7-dihydro-5,7-dimethyl-8H-pyrrolo[3,2-e]-s-triazolo[1,5-a]pyrimidine.

7. 6,7-Dihydro-8-(o-fluorobenzyl)-5-methyl-5-methyl-8-pyrrolo[3,2-e]-s-triazolo[1,5-a]pyrimidine.

8. 8-(o-Chlorobenzyl)-6,7-dihydro-5,7-dimethyl-8H-pyrrolo[3,2-e]-s-triazolo(1,5-a]pyrimidine.

9. 6,7-Dihydro-7-ethyl-8-(o-fluorobenzyl)-5-methyl-8H-pyrrolo[3,2-e]-s-triazolo[1,5-a]pyrimidine.

10. 6,7-Dihydro-5-methyl-8-(3,4,5-trimethoxybenzyl)-8H-pyrrolo[3,2-e]-s-triazolo[1,5-a]pyrimidine.

* * * * *

UNITED STATES PATENT AND TRADEMARK OFFICE
CERTIFICATE OF CORRECTION

PATENT NO. : 4,007,189
DATED : February 6, 1977
INVENTOR(S) : YASUNOBU SATO et al It is certified that error appears in the above-identified patent and that said Letters Patent are hereby corrected as shown below:

Column 6, line 6: replace "N, 29.64" with --- N, 20.64 ---.

Column 7, line 57: replace "4.5g" with --- 4.6 g ---.

Column 10, lines 61-62: replace "-5-methyl-5-methyl-8-pyrrolo" in Claim 7 with --- -5-methyl-8H-pyrrolo ---.

Signed and Sealed this

Thirteenth Day of September 1977

[SEAL]

Attest:

RUTH C. MASON
Attesting Officer

LUTRELLE F. PARKER
Acting Commissioner of Patents and Trademarks